United States Patent
Kleiner et al.

(10) Patent No.: US 6,229,044 B1
(45) Date of Patent: May 8, 2001

(54) ALKYL-1-ALKOXYETHYLPHOSPHINOUS ACID ALUMINUM SALTS

(75) Inventors: Hans-Jerg Kleiner, Kronberg; Elke Jenewein, Gersthofen; Wolfgang Wanzke, Meitingen, all of (DE)

(73) Assignee: Ticona GmbH Deutschland KG (DE)

( * ) Notice: Subject to any disclaimer, the term of this patent is extended or adjusted under 35 U.S.C. 154(b) by 0 days.

(21) Appl. No.: 09/380,667

(22) PCT Filed: Feb. 20, 1998

(86) PCT No.: PCT/EP98/00980

§ 371 Date: Nov. 17, 1999

§ 102(e) Date: Nov. 17, 1999

(87) PCT Pub. No.: WO98/39339

PCT Pub. Date: Sep. 11, 1998

(30) Foreign Application Priority Data

Mar. 4, 1997 (DE) ................................................. 197 08 724

(51) Int. Cl.⁷ ....................................................... C07F 9/30
(52) U.S. Cl. .................................................. 562/23; 562/8
(58) Field of Search ........................................... 562/23, 8

(56) References Cited

U.S. PATENT DOCUMENTS

| | | |
|---|---|---|
| 3,594,347 | 7/1971 | Lazarus et al. . |
| 3,892,347 | 7/1975 | Tsui et al. . |
| 3,900,444 | 8/1975 | Racky et al. . |
| 3,953,539 | 4/1976 | Kawase et al. . |
| 4,036,811 | 7/1977 | Noetzel et al. . |
| 4,049,612 | 9/1977 | Sandler . |
| 4,078,016 | 3/1978 | Kramer . |
| 4,180,495 | 12/1979 | Sandler . |
| 4,208,321 | 6/1980 | Sandler . |
| 4,208,322 | 6/1980 | Sandler . |
| 5,196,554 * | 3/1993 | Svara ..................................... 556/13 |
| 5,780,534 * | 7/1998 | Kleiner et al. ........................ 524/133 |

FOREIGN PATENT DOCUMENTS

| | | |
|---|---|---|
| 700 042 | 7/1967 | (BE) . |
| 2 102 841 | 8/1971 | (DE) . |
| 2 252 256 | 5/1974 | (DE) . |
| 2 252 258 | 5/1974 | (DE) . |
| 2 447 727 | 4/1976 | (DE) . |
| 2 915 116 | 11/1979 | (DE) . |
| 006 568 | 1/1980 | (EP) . |
| 2 827 867 | 1/1980 | (DE) . |
| 452 755 | 10/1991 | (EP) . |
| 458067 | 11/1991 | (EP) . |
| 699 708 | 3/1996 | (EP) . |
| 794 191 | 9/1997 | (EP) . |
| 2 204 659 | 10/1972 | (FR) . |
| 2 422 698 | 4/1978 | (FR) . |

OTHER PUBLICATIONS

Derwent English Abstract (1971–52012S) for DE 2 102 841 (Aug. 5, 1971).
Derwent English Abstract (1974–C6071V) for DE 2 252 256 (May 9, 1974).
Derwent English Abstract (1974–34563V) for DE 2 252 258 (May 9, 1974).
Derwent English Abstract (1976–28565X) for DE 2 447 727 (Apr. 8, 1976).
Derwent English Abstract (1979–59863B) for DE 2 915 116 (Oct. 25, 1979).
Derwent English Abstract (1980–02156C) for DE 2 827 867 (Jan. 17, 1980).
Derwent English Abstract (1980–02156C) for EP 006 568 (Jan. 9, 1980).
Derwent English Abstract (1991–312407) for EP 452 755 (Oct. 23, 1991).
Derwent English Abstract (1991–347511) for EP 458 067 (Nov. 27, 1991).
Derwent English Abstract (1996–130732) for EP 699 708 (Mar. 6, 1996).
Derwent English Abstract (1997–437433) for EP 794 191 (Sep. 10, 1997).
Derwent English Abstract (1974–34563V) for FR 2 204 659 (Oct. 25, 1972).
Derwent English Abstract (1979–59863B) for FR 2 422 698 (Apr. 13, 1978).
Derwent English Abstract (1976–42858X) for JP 51 047035 and JP 82 059262 (Apr. 22, 1976).
English Abstract for BE 700,042 Jan. 12, 1967.

* cited by examiner

Primary Examiner—Jean F. Vollano
(74) Attorney, Agent, or Firm—Connolly Bove Lodge & Hutz LLP

(57) ABSTRACT

Aluminum salts of alky-(1-alkoxyethyl)phosphinic acids are prepared by reacting alky-(1-alkoxyethyl)phospihnic acids with aluminum hydroxide in a molar ratio of 3:1. The resulting aluminum phosphinates are used as flame retardants in thermoplastics, particularly in polyesters.

11 Claims, No Drawings

ALKYL-1-ALKOXYETHYLPHOSPHINOUS ACID ALUMINUM SALTS

This is the natural phase of PCT/EP98/00980, filed 2/20/1998, now WO 98/39339.

BACKGROUND OF THE INVENTION

1. Field of the Invention

The invention relates to novel aluminum salts of alkyl-(1-alkoxyethyl)-phosphinic acids, their preparation and their use as flame retardants.

2. Description of the Prior Art

Polymers are frequently made flame retardant by adding to them phosphorus-containing or halogen-containing compounds or mixtures thereof. Some polymers are processed at high temperatures, e.g. at 250° C. or above. For this reason, many known flame retardants are not suitable for such applications, because they are too volatile or are not sufficiently heat-stable.

Alkali metal salts of dialkylphosphinic acids are thermally stable and are already proposed as flame retardant additives for polyester (DE-A1-2 252 258). They must be introduced in amounts of up to 30% by weight and some have an adverse corrosion-promoting effect on the processing machinery.

Furthermore, the salts of dialkylphosphinic acids with an alkali metal or a metal from the second or third main group or subgroup of the Periodic Table of the Elements have been used for the preparation of flame-resistant polyamide molding compositions, in particular the zinc salts (DE-A1-2 447 727). Low-flammability thermoplastics may also be prepared by using said salts of phosphinic acids in combination with nitrogen bases such as melamine, dicyandiamide or guanidine (DE-A1-28 27 867).

A further large class of salts of phosphinic acid are the polymeric metal phosphinates. These are nonionic coordination complexes and are soluble in organic solvents. They are suitable as flame retardant components for halogenated aromatic polymers and for polyesters (U.S. Pat. Nos. 4,078, 016; 4,180,495), polyamides (U.S. Pat. No. 4,208,321) and polyester/polyamides (U.S. Pat. No. 4,208,322).

Dialkylphosphinic acids are prepared by free-radically catalyzed addition of olefins onto phosphonous acid monoesters and the subsequent hydrolysis of the dialkylphosphinic esters thus produced. Monoesters of phosphonous acid are produced from phosphonous acids. These are obtained by hydrolysis of dichlorophosphines. The processes are technically complex and proceed over a plurality of stages. Industrially simple preparation processes for salts of phosphinic acids which start from dichlorophosphines are therefore sought.

SUMMARY OF THE INVENTION

The object is achieved by novel aluminum salts of alkyl-(1-alkoxyethyl)-phosphinic acids of the formula (I)

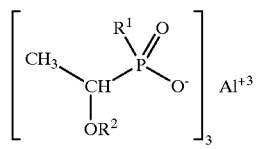

where $R^1$ is an unbranched or branched alkyl radical having 1 to 6 carbon atoms, preferably methyl, ethyl, n-propyl, isopropyl, n-butyl or tert-butyl, and $R^2$ is an unbranched or branched alkyl radical having 1 to 4 carbon atoms, preferably methyl or ethyl, and a process for preparing the aluminum salts of the formula (I), which comprises reacting alkyl-(1-alkoxyethyl)phosphinic acids of the formula (II)

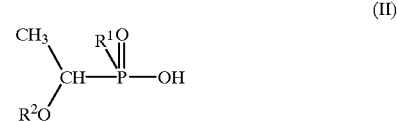

with aluminum hydroxide in a molar ratio of approximately 3:1.

DESCRIPTION OF THE PREFERRED EMBODIMENTS

The phosphinic acids of the formula (II) are prepared by known methods from alkyldichlorophosphines and acetaldehyde diacetals (V.S. Tsivunin et al., Zh. Obshch. Khim. 40 (102) 1970, 12, 2560 (1970).

For example, alkyldichlorophosphine is reacted with acetaldehyde diacetal to give alkyl-(1-alkoxyethyl) phosphinic chloride, which is then hydrolyzed to give the corresponding phosphinic acid. The phosphinic acids formed are then reacted in a known manner (EP-A-699 708) with aluminum hydroxide in a molar ratio of 3:1. In this reaction the phosphinic acid and the aluminum hydroxide are stirred in water at 80–100° C. until the aluminum phosphinate according to the invention has been formed virtually quantitatively. Preferably, the reaction is carried out in suitable solvents or solvent mixtures, e.g. in glacial acetic acid. To reduce the duration of the reaction, it is also possible to carry out the preparation of the salts of phosphinic acid according to the invention under pressure at temperatures of 110–250° C.

The salts of phosphinic acid, after drying well, preferably under reduced pressure at temperatures of 150–200° C., are used as flame retardants for polymer molding compositions, e.g. for polyesters such as poly(butylene terephthalate).

Polyesters are polymers which contain repeating units bound via an ester group in the polymer chain. Polyesters which can be used according to the invention are described, for example, in "Ullmann's encyclopedia of industrial chemistry", ed. Barbara Eivers, Vol. A21, Chapter 'Polyesters' (pp. 227–251), VCH, Weinheim-Basle-Cambridge-New York 1992, which is incorporated herein by reference.

The amount of the salt of phosphinic acid of the formula (I) to be added to the polymer can vary within broad limits. Generally, 5 to 30% by weight are used, based on the polymer. The optimum amount depends on the nature of the polymer and on the type of the salt of phosphinic acid used and can readily be determined by experiments.

The salts of phosphinic acid according to the invention can be used in various physical forms, depending on the type of the polymer used and on the desired properties. Thus, for example to achieve an enhanced dispersion in the polymer, the salts of phosphinic acid can be ground to give a finely particulate form. If desired, mixtures of different salts of phosphinic acid can also be used.

The salts of phosphinic acid according to the invention are thermally stable, and neither decompose the polymers during processing nor affect the production process of the polyester molding composition. The salts of phosphinic acid are not volatile under preparation and processing conditions for polymers.

The salt of phosphinic acid can be incorporated into the polymer by mixing the two and then melting the polymer in a compounding unit (e.g. in a twin-screw extruder) and homogenizing the salt of phosphinic acid in the polymer melt. The melt can be taken off as extrudate, cooled and granulated. The salt of phosphinic acid can also be metered directly into the compounding unit.

It is also possible to admix the flame-retardant additives to finished polyester granules and process the mixture directly on an injection molding machine or to melt the flame-resistant additives in advance in an extruder, to granulate them and process them after a drying process.

The flame-retardant additive can also be added during the polycondensation. In addition to salts of phosphinic acid according to the invention, fillers and reinforcing agents such as glass fibers, glass beads or minerals such as chalk can be added to the formulations. In addition, the products can comprise other additives, such as stabilizers, lubricants, colorants, nucleating agents or antistatics.

The low-flammability polyesters according to the invention are suitable for the preparation of shaped bodies, films, filaments and fibers, e.g. by injection molding, extrusion or pressing.

EXAMPLES

1. Preparation of 1-methoxyethyl(methyl)phosphinic Acid
   1.1. Preparation of the acid chloride
   649 g (5.55 mol) of dichloromethylphosphine were heated to 30° C. and 500 g (5.55 mol) of acetaldehyde dimethyl acetal were added dropwise at 30–40° C. in the course of 3.5 hours with stirring and cooling. In the course of this, methyl chloride was formed vigorously. After completion of gas formation, the mixture was heated briefly to 60° C., then cooled and stirred further. The mixture was then distilled. 548 g of 1-methoxyethyl(methyl)phosphinic chloride were obtained at a boiling temperature of 63° C. at 0.25 mbar. This corresponds to a yield of 64% of theory.
   1.2. Preparation of the Acid
   126.1 g (7 mol) of water were added carefully dropwise with cooling and stirring to 547.6 g (3.5 mol) of 1-methoxyethyl(methyl)-phosphinic chloride. After addition was complete, the mixture was agitated at room temperature and then distilled. 471 g were obtained at a boiling temperature of 135–138° C. at 0.1 mbar. This corresponds to a yield of 97.5% of theory.
2. Preparation of the Aluminum salt of 1-methoxyethyl (methyl)-phosphinic Acid
   345 g (2.5 mol) of 1-methoxyethyl(methyl)phosphinic acid were dissolved in 1.2 l of water and stirred with 65 g (0.83 mol) of aluminum hydroxide for 72 hours at 80–90° C. The mixture was filtered off using suction, washed with water and dried at 0.5 mbar, initially at 80° C. and then at 180° C. 334 g of a white powder which does not melt at 350° C. were obtained. This corresponds to a yield of 92% of theory.

| Result of elemental analysis: | | | $C_{12}H_{30}AlO_9P_3$ (438) | |
|---|---|---|---|---|
| calculated: | 32.9% C | 6.85% H | 6.17% Al | 21.23% P |
| found: | 33.0% C | 7.05% H | 5.9% Al | 20.9% P |

3. Preparation of 1-ethoxyethyl(methyl)phosphinic acid
   3.1. Preparation of the Acid Chloride
   96.1 g (0.82 mol) of dichloromethylphosphine were cooled to −20° C. and 97 g (0.82 mol) of acetaldehyde diethyl acetal were added dropwise in the course of 3.5 hours with stirring and constant cooling. After dropwise addition was complete, the mixture was allowed to come to room temperature and was further stirred for two hours. The mixture was then distilled. 87 g of 1-ethoxyethyl(methyl)-phosphinic chloride were obtained at a boiling temperature of 65° C. at 0.75 mbar. This corresponds to a yield of 62% of theory.
   3.2. Preparation of the Acid
   18 g (1.0 mol) of water were carefully added dropwise to 34 g (0.2 mol) of 1-ethoxyethyl(methyl)phosphinic chloride at 10° C. with cooling and stirring. After addition was complete, the mixture was further stirred for one hour at room temperature and then distilled. 29.5 g were obtained at a boiling temperature of 136–138° C. at 0.35 mbar. This corresponds to a yield of 97% of theory.
4. Preparation of the Aluminum salt of 1-ethoxyethyl (methyl)phosphinic Acid
   297 g (1.95 mol) of 1-ethoxyethyl(methyl)phosphinic acid and 50.7 g (0.65 mol) of aluminum hydroxide were stirred in 1.2 l of water for 75 hours at 80–90° C. The mixture was then filtered off using suction, rinsed with water and dried at 0.5 mbar, initially at 80° C. then at 180° C. 265 g of a white powder having a residual water content of 0.06% were obtained. The melting point is above 350° C. This corresponds to a yield of 85% of theory.

| Result of elemental analysis: | | | $C_{15}H_{36}AlO_9P_3$ (480) | |
|---|---|---|---|---|
| calculated: | 37.5% C | 7.5% H | 5.69% Al | 19.38% P |
| found: | 36.9% C | 7.4% H | 5.5% Al | 19.4% P |

5. Preparation of 1-methoxyethyl(ethyl)phosphinic Acid
   5.1. Preparation of the acid chloride
   143.8 g (1.098 mol) of dichloroethylphosphine were cooled to −10 to 15° C. and 99 g (1.099 mol) of acetaldehyde dimethyl acetal were added dropwise in the course of 90 minutes. The mixture was allowed to come to room temperature slowly. It was then further stirred for 24 hours and then distilled. 119 g of 1-methoxyethyl-(ethyl) ethylphosphinic chloride were obtained at a boiling temperature of 69° C. at 0.6 mbar. This corresponds to a yield of 60% of theory.
   5.2. The acid was prepared in a similar manner to the instructions of 1.2 1-Methoxyethyl(ethyl)phosphinic acid having a boiling point of 146–151° C. at 0.25 mbar were obtained in approximately 95% yield.
6. Preparation of the Aluminum Salt of 1-methoxyethyl (ethyl)phosphinic Acid
   127 g (0.84 mol) of 1-methoxyethyl(ethyl)phosphinic acid were stirred in 400 ml of water with 21.7 g (0.278 mol) of aluminum hydroxide for 72 hours at 80–90° C. The mixture was then filtered off using suction, washed with water and dried at 0.5 mbar, initially at 80° C. then at 180° C. 96 g of a white powder which does not melt at up to 350° C. were obtained. This corresponds to a yield of 72% of theory.

| Result of elemental analysis: | | | $C_{15}H_{36}AlO_9P_3$ (480) | |
|---|---|---|---|---|
| calculated: | 37.5% C | 7.5% H | 5.63% Al | 19.38% P |
| found: | 37.5 %C | 7.1% H | 5.3% Al | 20.0% P |

7. Use Example
   From the aluminum salt of 1-methoxyethyl(methyl) phosphinic acid, prepared as described in Example 2, and poly(butylene terephthalate), compounds reinforced with 30% glass fibers were produced without other additives, test pieces of thickness 1.5 mm were extruded and tested with the following result:

| Concentration % | Flammability rating UL 94 |
|---|---|
| 20 | V1 |

What is claimed is:

1. An aluminum salt of an alkyl (1-alkoxyethyl) phosphinic acid of formula (I):

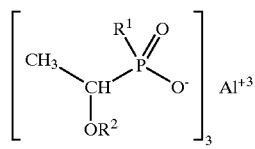

where $R^1$ is an alkyl group having 1 to 6 carbon atoms, and $R^2$ is an alkyl group having 1 to 4 carbon atoms.

2. A process for preparing the aluminum salt as claimed in claim 1, which comprises reacting an alkyl-(1-alkoxyethyl)phosphinic acid of the formula II:

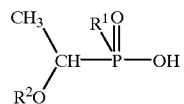

where $R^1$ and $R^2$ are defined as in formula (I), with aluminum hydroxide.

3. The process as claimed in claim 2, wherein the alkyl-(1-alkoxyethyl)phosphinic acid to aluminum hydroxide are present in a molar ratio of approximately 3:1.

4. The process as claimed in claim 2, wherein the reaction is carried out under a pressure and at a temperature of from 110 to 250° C.

5. The aluminum salt as claimed in claim 1, wherein $R^1$ is a methyl, ethyl, n-propyl, isopropyl, n-butyl or tert-butyl group.

6. The aluminum salt as claimed in claim 2, wherein $R^1$ is a methyl, ethyl, n-propyl, isopropyl, n-butyl or tert-butyl group.

7. The aluminum salt as claimed in claim 1, wherein $R^2$ is a methyl or ethyl group.

8. The aluminum salt as claimed in claim 2, wherein $R^2$ is a methyl or ethyl group.

9. The process according to claim 2, wherein the reaction is carried out in a solvent.

10. The process according to claim 9, wherein the solvent is water or glacial acetic acid.

11. The aluminum salt as claimed in claim 5, wherein $R^2$ is a methyl or ethyl group.

* * * * *